(12) United States Patent
Dindi et al.

(10) Patent No.: US 8,115,007 B2
(45) Date of Patent: Feb. 14, 2012

(54) SYNTHESIS OF DIAMINODINITROPYRIDINE

(75) Inventors: Hasan Dindi, Wilmington, DE (US); James Arnold Schultz, Swedesboro, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1069 days.

(21) Appl. No.: 11/986,877

(22) Filed: Nov. 27, 2007

(65) Prior Publication Data

US 2009/0137814 A1 May 28, 2009

(51) Int. Cl.
*C07C 211/00* (2006.01)
*C07D 213/72* (2006.01)

(52) U.S. Cl. ........................ 546/307; 564/306

(58) Field of Classification Search .......... None
See application file for complete search history.

(56) References Cited

U.S. PATENT DOCUMENTS

| | | | |
|---|---|---|---|
| 3,740,410 | A | 6/1973 | Gerber |
| 3,838,154 | A | 9/1974 | Gerber |
| 4,022,793 | A | 5/1977 | Gerber |
| 4,950,302 | A | 8/1990 | Clausen et al. |
| 5,674,969 | A | 10/1997 | Sikkema et al. |
| 5,945,537 | A | 8/1999 | Sikkema |

FOREIGN PATENT DOCUMENTS

| | | |
|---|---|---|
| DE | 3920336 | 1/1997 |
| SU | 1066992 | 1/1984 |
| WO | WO 94/25506 | 11/1994 |
| WO | 2006/105080 A | 10/2006 |
| WO | 2006/105227 A | 10/2006 |

OTHER PUBLICATIONS

Sikkema D J: "Design, synthesis and properties of a novel rigid rod polymer, PIPD or 'M5': high modulus and tenacity fibres with substantial compressive strength", Polymer, Elsevier Science Publishers B.V., GB, vol. 39, No. 24, Nov. 1, 1998.
Williams R . et al : "The chemistry of aryltetraamines. II. The synthesis of 2,3,5,6-tetraaminopyridine", Journal of Heterocyclic Chemistry, Heterocorporation. RPOVO, US, vol. 8, Jan. 1, 1971.
Database Beilstein, Beilstein Institute for Organic Chemistry, Frankfurt-Main, DE: XP002515309, retrieved from Beilstein Database accession No. 22062278 abstract and Journal of the Chemical Society, 1934, p. 243.
Licht et al., New explosives: dinitropyridine; International Annual Conference of ICT (1993), 24th (Energetic Materials: Insensitivity and Environmental Awareness), Jun. 1-8, German Journal. Abstract.
Ritter et al., Synthesis of reactions of dinitrated amino and diaminopyridines; J. of Heterocyclic Chemsity (1995), 32(2), 585-90; Pub.: HeteroCorporation. Abstract.
Hollins et al., 2, 6-Diamino-3,5-dinitropyridine-1-oxide—A new insensitive explosive; Report (1995), NAWC-WPNS-TP-8828, Order No. AD-A29799/5GAR, 35 pp. From: Gov. Rep. Announce. Index (U.S.) 1996, 96(4), Abstr. No. 04-02, 188. Abstract.
Hollins et al., Aminonitroheterocyclic N-oxides—a new class of insensitive energetic materials; Materials Research Society Symposium Proceedings (1996), 418 (Decomposition, Combustion, and Detonation Chemistry of Energetic Materials), 31-6. Pub.: Materials Research Society. Abstract.
Hollins et al., Aminonitropyridines and their N-oxides; J. of Heterocyclic Chemistry (1996), 33(3), 895-904. Pub.: HeteroCorporation. Abstract.
Jalovy et al., New energetic materials of N-heterocyclic group; Scientific Papers of the University of Pardubice, Series A: Faculty of Chemical Technology (2004), Volume Date 2003, 9, 197-196. Pub.: University of Pardubice. Abstract.

*Primary Examiner* — Janet Andres
*Assistant Examiner* — Heidi Reese

(57) ABSTRACT

A process for the preparation of diaminodinitropyridine or diaminodinitrobenzene by contacting an aminopyridine or aminobenzene with oleum and nitric acid, wherein the improvement comprises adding at least about 1% molar excess of nitric acid, based upon the aminopyridine or aminobenzene with stirring for at least two hours to form first the intermediate sulfonic acid, and then diaminodinitropyridine or diaminodinitrobenzene, and use of such products in the preparation of rigid rod polymers is disclosed.

11 Claims, No Drawings

SYNTHESIS OF DIAMINODINITROPYRIDINE

BACKGROUND OF THE INVENTION 2,6-Diamino-3,5-dinitropyridine and diaminodinitrobenzene are intermediates for the preparation of precursors for the manufacture of "rigid rod" polymers used in fabricating films, filaments, and yarns. An example of such rigid rod polymers, poly[pyridobisimidazole-2,6-diyl(2,5-hydroxy-p-phenylene) or poly(2,3,5,6-tetraminopyridine-co-2,5-dihydroxyterephthalate) is described by Sikkema et al. in U.S. Pat. No. 5,674,969. 2,6-Diamino-3,5-dinitropyridine can also be used as an insensitive (safe) explosive and as a multifunctional organic reagent.

2,6-Diamino-3,5-dinitropyridine is prepared by nitration of 2,6-diaminopyridine. The nitration of 2,6-diaminopyridine by reaction with a mixture of nitric acid and sulfuric acid is known from German Patent 3,920,336. The drawback to this process is that it gives a 2,6-diamino-3,5-dinitropyridine yield of not more than 50% of theory.

Sikkema et al. in U.S. Pat. No. 5,945,537 describe an improved process for the conversion of 2,6-diaminopyridine to 2,6-diamino-3,5-dinitropyridine in a single step reaction using oleum (fuming sulfuric acid). The diaminopyridine is added to the oleum, and then concentrated nitric acid is added, and the product isolated. A yield improvement to more than 90% was obtained.

The prior art processes for the production of 2,6-diamino-3,5-dinitropyridine and the corresponding diaminodinitrobenzene are prone to yield product containing variable amounts of heretofore-unidentified impurities. The composition of the impurities and the effect of these impurities on products made using the 2,6-diamino-,5-dinitropyridine and the corresponding diaminodinitrobenzene are unknown.

It is desirable to find a nitration process for the preparation of diaminodinitropyridine and diaminodinitrobenzene that provides a high yield free of impurities. It is also desirable to identify the composition of the impurities. It is also desirable to find a process of making rigid rod polymers having a minimum inherent viscosity of about 25 dL/g. The present invention identifies one of the major impurities and provides such processes.

SUMMARY OF THE INVENTION

The present invention comprises a process for the preparation of 1) diaminodinitropyridine or 2) diaminodinitrobenzene by contacting 1) an aminopyridine or 2) an aminobenzene, respectively, with oleum and nitric acid, wherein the improvement comprises adding at least about 1% molar excess of nitric acid based upon the aminopyridine or aminobenzene respectively, with stirring for at least two hours to form first 1) aminonitropyridine sulfonic acid or 2) aminonitrobenzene sulfonic acid, respectively, and then 1) diamino-dinitropyridine or 2) diaminodinitrobenzene respectively.

The present invention further comprises a composition comprising 2,6-diamino-3-nitropyridine-5-sulfonic acid.

The present invention further comprises a process for purification of 1) diaminodinitropyridine which contains 2,6-diamino-3-nitropyridine-5-sulfonic acid or 2) diaminodinitrobenzene which contains 2,6-diamino-3-nitrobenzene-5-sulfonic acid comprising contacting 1) said diaminodinitropyridine or 2) said diaminodinitrobenzene respectively with oleum and at least about 1% molar excess of nitric acid based upon the diaminodinitropyridine or diaminodinitrobenzene, with stirring for at least two hours to yield 1) diaminodinitropyridine having less than about 0.1% by weight of 2,6-diamino-3-nitropyridine-5-sulfonic acid or 2) diaminodinitrobenzene having less than about 0.1% by weight of 2,6-diamino-3-nitrobenzene-5-sulfonic acid respectively.

The present invention further comprises a process for the preparation of poly(2,3,5,6-tetraminopyridine-co-2,5-dihydroxyterephthalate) having an inherent viscosity of at least 25 dL/g comprising
  A) hydrogenation of diaminodinitropyridine which contains less than about 0.1% by weight of 2,6-diamino-3-nitropyridine-5-sulfonic acid to yield tetraminopyridine,
  B) coupling of said tetraminopyridine with dipotassium dihydroxyterephthalate to yield a tetraminopyridinium dipotassium dihydroxyterephthalate complex, and
  C) polymerization of said tetraminopyridinium dipotassium dihydroxyterephthalate complex to yield poly(2,3,5,6-tetraminopyridine-co-2,5-dihydroxyterephthalate) having an inherent viscosity of at least 25 dL/g.

The present invention further comprises a process for the preparation of poly(2,3,5,6-tetraminobenzene-co-2,5-dihydroxyterephthalate) having an inherent viscosity of at least 25 dL/g comprising
  A) hydrogenation of diaminodinitrobenzene which contains less than about 0.1% by weight of 2,6-diamino-3-nitrobenzene-5-sulfonic acid to yield tetraminobenzene,
  B) coupling of said tetraminobenzene with dipotassium dihydroxyterephthalate to yield a tetraminobenzene dipotassium dihydroxyterephthalate complex, and
  C) polymerization of said tetraminobenzene dipotassium dihydroxyterephthalate complex to yield poly(2,3,5,6-tetraminobenzene-co-2,5-dihydroxyterephthalate) having an inherent viscosity of at least 25 dL/g.

DETAILED DESCRIPTION

Trademarks are denoted herein by capitalization. Chemical abbreviations used herein are shown in Table 1.

TABLE 1

Chemical Abbreviations

| Abbreviation | Chemical name |
| --- | --- |
| DADNP | 2,6-diamino-3,5-dinitropyridine |
| DANPS | 2,6-diamino-3-nitropyridine-5-sulfonic acid |
| DAP | 2,6-diaminopyridine |
| DAPH | 2,6-diaminopyridine hemisulfate |
| DAPSA | 2,6-diaminopyridine-3-sulfonic acid |
| HADNP | 2-hydroxy-6-amino-3,5-dinitropyridine |
| $K_2$-DHTA | dipotassium dihydroxyterephthalate |
| M5 Monomer | Tetraaminopyridinium dipotassium dihydroxyterephthalate complex |
| M5 Polymer | poly(2,3,5,6-tetraaminopyridine-co-2,5-dihydroxyterephthalate) |
| TAP | 2,3,5,6-tetraaminopyridine |
| TAP/$K_2$-DHTA complex | Tetraaminopyridinium dipotassium dihydroxyterephthalate complex, Synonym for M5 Monomer |
| DMAC | Dimethylacetamide |
| THF | Tetrahydrofuran |

The present invention comprises a process for the preparation of aminonitropyridines and aminonitrobenzenes from aminopyridines and aminobenzenes respectively. Specifically, 2,6-diamino-3,5-dinitropyridine is prepared from 2,6-diaminopyridine or its neutralization product with sulfuric acid, 2,6-diaminopyridine hemisulfate. The reaction is conducted by contacting 2,6-diaminopyridine (DAP) or 2,5-diaminopyridine hemisulfate (DAPH) with oleum and concentrated nitric acid with stirring for at least two hours. The 2,6-diamino-3,5-dinitropyridine produced by the method of the present invention is purer than that produced by the method of the prior art, free of a harmful byproduct, and yields purer 2,3,5,6-tetraminopyridine, an intermediate in the preparation of rigid rod polymers, such as poly(2,3,5,6-tetraminopyridine-co-2,5-dihydroxyterephthalate) (M5 Polymer). The M5 Polymer thereby produced has a higher inherent viscosity (IV) and increased tenacity, measured as g (force)/denier or g (force)/tex. For high strength fiber a high tensile strength is desired. For M5 Polymer a value of 35-40 g (force)/denier is desired.

The improved nitration process of the present invention can also be utilized for the nitration of m-diaminobenzene to provide diamino-dinitrobenzene. Hydrogenation of the latter product forms 1,2,4,5-tetramino benzene, the intermediate for a similar rigid rod copolymer, poly(1,2,4,5-tetraminobenzene-co-2,5-dihydroxyterephthalate). Improvements in the tetraminobenzene and end product copolymer result from the use of the process of the present invention, as is the case with the 2,6-diaminopyridine process.

In the following discussion and examples, the diaminodinitropyridines will be detailed. All such details also apply to the preparation and use of diaminodinitrobenzenes.

It has been found that the process involves a sequence of reactions starting from 2,6-diaminopyridine (DAP) to form a first sulfonic acid intermediate, 2,6-diaminopyridine-3-sulfonic acid (DAPSA) that is readily nitrated to a second sulfonic acid intermediate, 2,6-diamino-3-nitropyridine-5-sulfonic acid (DANPS). While the initial formation of 2,6-diaminopyridine hemisulfate (DAPH) during the nitration of DAP is known, the fact that this nitration proceeds through the intermediate compound 2,6-diamino-3-nitropyridine-5-sulfonic acid (DANPS) in the synthesis of 2,6-diamino-3,5-dinitropyridine (DADNP) has not been previously recognized or reported. The relatively rapid formation of DANPS is followed by a slower nitration of DANPS to DADNP. For this last reaction to be completed, the reaction mixture must be stirred at ambient temperature for about 2 to about 4 hours, preferably about 4 hours. The reactions are shown in Reaction Sequence 1.

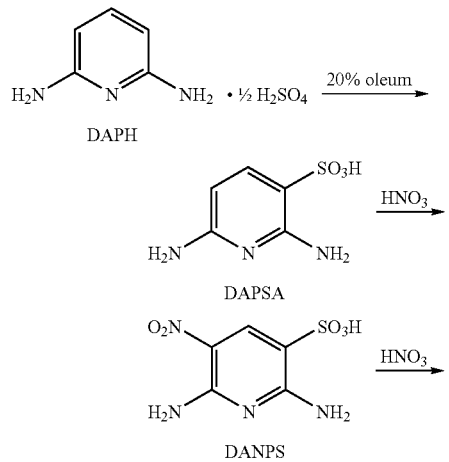

DADNP 2,6-Diaminopyridine-3-sulfonic acid (DAPSA) is formed when 2,6-diaminopyridine (DAP), or 2,6-diaminopyridine hemisulfate salt (DAPH) is contacted with cold oleum. The oleum concentration is from about 10% to about 30% oleum and preferably about 20%. The oleum is added at a temperature of from about −5° C. to about 25° C., and preferably at from about 0° C. to about 10° C. Previously, it was incorrectly believed that this was a simple dissolution of the 2,6-diaminopyridine hemisulfate salt (DAPH) in the oleum. In the process of the present invention as concentrated (98%) nitric acid is added slowly to 2,6-diaminopyridine-3-sulfonic acid (DAPSA) in oleum solution, first 2,6-diamino-3-nitropyridine-5-sulfonic acid (DANPS) is readily formed from the first stoichiometric amount of nitric acid. As the second stoichiometric amount of concentrated (98%) nitric acid is added, a second nitro group replaces the sulfonic acid group to form 2,6-diamino-3,5-dinitropyridine (DADNP). The second nitration is a slower step. In the process of the present invention, a small excess of nitric acid is used but the reaction is stirred for a time sufficient for the sulfonic acid group to be totally displaced. Typically this is from about 2 to about 4 hours at a temperature of from about 5° C. to about 30° C., and preferably from about 20° C. to about 25° C. The nitric acid can be added in increments or in a single or continuous addition. Only a small excess of nitric acid (about 1 to 3%) is necessary to completely remove the sulfonic acid group. Prolonged stirring at ambient temperature is employed.

The importance of the formation of this intermediate is that DANPS as a residual contaminant in DADNP adversely affects the quality of subsequent products made using the DADNP. In the prior art, the importance of the length of the stirring period was not recognized, consequently the 2,6-diamino-3,5-dinitropyridine (DADNP) product contained various residual amounts of 2,6-diamino-3-nitro-5-sulfonic acid (DAPSA). In turn M5 Polymer prepared from such compounds was highly variable and relatively poor quality. For the purposes of this patent, the appearance and quality of the M5 Polymer is a light purple color polymer having an inherent viscosity (IV) of at least 25 dL/g. Such higher IV values of the M5 Polymer provide higher quality fibers having higher breaking strength, (tenacity) measured as g(force)/denier. The DANPS content of the DADNP prepared by the method of the present invention is less than about 0.1%, and preferably less than about 0.05% by weight. The detection limit for DANPS by HPLC is approximately 0.05% by weight.

A second impurity that can occur when making diaminodinitropyridine (DADNP) by prior art methods is 2-hydroxy-6-amino-3,5-dinitropyridine (HADNP), formed by the hydrolysis of an amine group, a reaction enhanced by higher temperatures. While not desired, HADNP is typically removed during the hydrogenation and during the coupling steps employed to make M5 Polymer. HADNP is also sufficiently soluble in aqueous solutions of sulfuric acid and ammonium hydroxide that it is readily removed in filtration and washing steps. The HADNP content of the DADNP prepared by the method of the present invention is less than 1%, and preferably less than 0.5%, by weight. However, if the HADNP content after sulfuric acid and ammonium hydroxide treatment should still exceed 1%, this impurity can also reduce the inherent viscosity and fiber strength of the M5 Polymer made therefrom. High residual levels (greater than about 1%) of HADNP in DADNP are readily reduced below the 1% level either by recrystallizing the DADNP from hot dimethylacetamide (DMAC) or by treating the aqueous DADNP slurry with a 5% aqueous solution of potassium carbonate, followed by a water wash and drying of the relatively insoluble DADNP. An aqueous ammonium hydroxide solution can be substituted for the potassium carbonate solution. Example 3 hereinafter demonstrates the removal of residual HADNP. HADNP content is quantified by $^1$H NMR.

Similarly, residual sulfuric acid, mainly present as the pyridinium salt, is removed after neutralization with ammonium hydroxide in the subsequent hydrogenation step. Quantification of residual sulfuric acid as the pyridinium salt is conducted by proton NMR or base titration. Base titration results also include the sulfate equivalent of sulfonic acid impurities.

The process of the present invention provides a yield of about 90% to about 96%. The process of the present invention does not require the preparation and isolation of 2,6-diaminopyridine hemisulfate salt intermediate, although this remains as an option. The 2,6-diamino-3-nitro-sulfonic acid (DANPS) intermediate, undesired in the final diaminodinitropyridine product, need not be isolated as the prolonged stirring results in its reaction with nitric acid to form the desired diaminodinitropyridine product. Thus the process of the present invention does not have such intermediates present as impurities in the product that can contaminate downstream polymers and products made therefrom.

In making rigid rod polymers, such as the M5 Polymer, DADNP is hydrogenated to form tetraminopyridine, which is then coupled with dipotassium dihydroxyterephthalate to form a complex, followed by polymerization of the complex. It has also been found that DANPS in DADNP poisons the precious metal catalyst used in the hydrogenation step of 2,6-diamino-3,5-dinitropyridine to 2,3,5,6-tetraminopyridine. While not wishing to be bound by theory, it is believed that the presence of even small amounts (less than 0.25%) of the sulfonic acid intermediate DANPS during the hydrogenation causes the formation of dye-like diazo compounds, resulting from N—N dimerization of hydroxylamines during the reduction of 2,6-diamino-3,5-dinitropyridine to 2,3,5,6-tetraminopyridine. Once formed, removal of these diazo impurities is at best extremely difficult. The diazo impurities are believed to lead to a colored 2,3,5,6-tetraminopyridine solution, then to an orange-colored complex of 2,3,5,6-tetraminopyridine and dipotassium 2,5-dihydroxyterephthate (TAP/K$_2$-DHTA complex). The DANPS impurity also has the potential to act as a chain terminating or chain transfer agent, resulting in weak points in the polymer chain, and thus a weaker fiber with a low inherent viscosity (IV). Using the process of the prior art, IV values from about 4 dL/g to only as high as about 21 dL/g are obtained. The higher values in this prior art IV range are obtained only after the removal of DANPS before polymerization by purification steps using solvents such as tetrahydrofuran (THF), acetone, or dimethylformamide. Firstly, DADNP having IV values of 25 dL/g or greater are preferred and necessary for the preparation of high IV M5 Polymer; secondly, avoiding the need for the DANPS purification steps is strongly preferred. In the preparation of rigid rod polymer and fiber using 2,6-diamino-3,5-dinitropyridine prepared by the process of the present invention, the hydrogenation step to 2,3,5,6-tetraminopyridine proceeds faster, more completely, and with a smaller precious metal catalyst requirement. As indicated above, the presence of even small amounts of DANPS also appears to poison the supported platinum or rhodium precious metal catalyst. Polymer from 2,3,5,6-tetraminopyridine, prepared by the process of the present invention, has consistently resulted in high inherent viscosity values of 30 dL/g or more.

The process of the present invention is conducted in a suitably agitated reaction vessel made of glass, or other materials that are compatible with the reaction mixture. Stainless steel, such as SS304 or SS316 stainless steel, becomes passivated by the excess nitric acid and can be used. The reaction vessel is optionally equipped with a reflux condenser to condense sulfur trioxide. A dryer device is installed to prevent ingress of moisture. In larger scale processes, a closed, slightly pressurized, and nitrogen-purged reactor is used. The reaction vessel further comprises methods of heating and cooling, and a means for measuring the temperature of the reaction mass. The 2,6-diaminopyridine is slurried in an excess of 20% oleum at a temperature of about 5° C. to about 15° C., then cooled to about 0° C., in preparation for the next exothermic nitration reaction. The amount of 20% oleum is an amount sufficient to provide about a 10% excess of sulfur trioxide over the amount required to react with all the water in the 98% nitric acid and the water produced during the nitration reaction. A small excess of concentrated (98%) nitric acid is added slowly with stirring at a temperature not exceeding 15° C. The amount of nitric acid is an amount sufficient to provide about a 2% to about a 5% excess molar proportion of nitric acid based on the stoichiometric amount required for the nitration of the aminopyridine and the degree of substitution required. The reaction mass is stirred at 5° C. to 15° C. until the solids dissolve to give a homogeneous dark brown solution (for at least 15 minutes). The reaction mass is allowed to reach ambient temperature and stirred for from about 2 hours to about 4 hours (4 hours is preferred) to effect the second nitration. The reaction mass is then drowned in chilled (−10° to −20° C.) 20% sulfuric acid (about 25 to about 35 times the weight of the initial 2,6-diaminopyridine) at a temperature not exceeding 5° C., and preferably not exceeding 0° C. Deionized water (about 5 to about 10 times the weight of the initial 2,6-diaminopyridine) is added at room temperature, and the mix stirred for 1 hour. The drowned mass is then filtered at room temperature and the filter cake washed sequentially with deionized water, 5% aqueous NH$_3$ solution, and then deionized water. Each wash is between about 5 to about 10 times the weight of the initial 2,6-diaminopyridine). The solid product is dried by any suitable method, including but not limited to nitrogen blow and vacuum suction, centrifugation and the like. The yield of 2,6-diamino-3,5-dinitropyridine is about 95%.

Quenching the reaction mix in 20% H$_2$SO$_4$ is preferred for the precipitation of the 2,6-diamino-3,5-dinitropyridine since the 20% H$_2$SO$_4$ gives a larger particle size versus quenching in water, facilitating the filtration, washing, and drying.

In a second embodiment, the present invention further comprises the composition 2,6-diamino-3-nitropyridine-5-sulfonic acid (DANPS). This is the intermediate formed during the process of the present invention described above, which is undesirable in the diaminodinitropyridine product. 2,6-Diamino-3-nitropyridine-5-sulfonic acid is prepared by dissolving 2,6-diaminopyridine or 2,6-diaminopyridine hemisulfate salt in oleum to form 2,6-diaminopyridine-3- sulfonic acid and treating the resulting solution with one stoichiometric amount of concentrated (98%) nitric acid. The resulting 2,6-diamino-3-nitropyridine-5-sulfonic acid is isolated by slowly drowning the reaction mix in an excess of 20% sulfuric acid followed by filtration, and washing the filter cake with water and 5% aqueous ammonium hydroxide solution and drying. 2,6-Diamino-3-nitropyridine-5-sulfonic acid is useful as a chemical intermediate, for instance as a dye intermediate.

The present invention further comprises 2,6-diamino-3,5-dinitropyridine prepared by the process of the present invention as described above, containing (i) less than 0.1%, and preferably less than 0.05%, DANPS; and (ii) less than 1%, and preferably less than 0.5%, HADNP.

The present invention further comprises a process for purification of 1) diaminodinitropyridine which contains 2,6-diamino-3-nitropyridine-5-sulfonic acid or 2) diaminodinitrobenzene which contains 2,6-diamino-3-nitrobenzene-5-sulfonic acid comprising contacting 1) said diaminodinitropyridine or 2) said diaminodinitrobenzene respectively with oleum and at least about 1% molar excess of nitric acid based upon the diaminodinitropyridine or diaminodinitrobenzene, with stirring for at least two hours to yield 1) diaminodinitropyridine having less than about 0.1% by weight of 2,6-diamino-3-nitropyridine-5-sulfonic acid or 2) diaminodinitrobenzene having less than about 0.1% by weight of 2,6-diamino-3-nitrobenzene-5-sulfonic acid respectively.

Thus the process of the present invention as described above can be used for renitration of diaminodinitropyridine which is contaminated with or contains 2,6-diamino-3-nitropyridine-5-sulfonic acid (DANPS), or renitration of diaminodinitrobenzene which is contaminated with or contains 2,6-diamino-3-nitrobenzene-5-sulfonic acid. Such contaminated diaminodinitropyridine or diaminodinitrobenzene is used as the starting material in the process using the same conditions as previously described above. The renitration or purification process of the present invention typically yields diaminodinitropyridine containing less than 0.1%, and preferably less than 0.05%, of DANPS, or diaminodinitrobenzene containing less than 0.1%, preferably less than 0.05%, of 2,6-diamino-3-nitrobenzene-5-sulfonic acid.

The present invention further comprises a process for making rigid rod polymers, in particular M5 Polymer, using diaminodinitropyridine prepared using the processes of the present invention as described above. Because such diaminodinitropyridine is free of, or contains less than 0.1% of, DANPS the rigid rod polymer obtained has an inherent viscosity of at least 25 dL/g. The process of the present invention for making M5 Polymer comprises:

A) hydrogenation of diaminodinitropyridine which contains less than about 0.1% by weight of 2,6-diamino-3-nitropyridine-5-sulfonic acid to yield tetraminopyridine, B) coupling of said tetraminopyridine with dipotassium dihydroxyterephthalate to yield a tetraminopyridinium dipotassium dihydroxyterephthalate complex, and C) polymerization of said tetraminopyridinium dipotassium dihydroxyterephthalate complex to yield poly(2,3,5,6-tetraminopyridine-co-2,5-dihydroxyterephthalate) having an inherent viscosity of at least 25 dL/g.

The complex formed in step B) above is also called the M5 Monomer and has the following structure of Formula 1. The final M5 Polymer has the structure of Formula 2 below wherein n is the degree of polymerization.

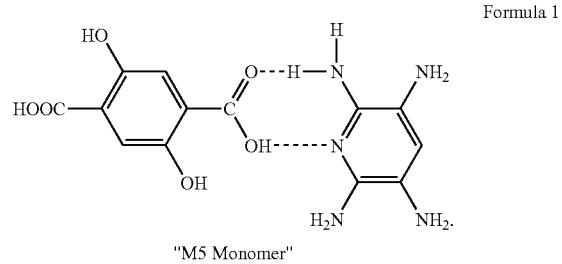

"M5 Monomer" Formula 1

"M5 Polymer" Formula 2

Tetraminopyridinium dipotassium dihydroxyterephthalate complex (M5 Monomer) is prepared by adding an aqueous solution of tetraminopyridine to an alkaline solution of dipotassium 2,5-dihydroxyterephthate. The preparation is performed with rigorous exclusion of oxygen, using de-aerated deionized water and a nitrogen purge. The M5 Monomer precipitates and is filtered. The preparation of the M5 Monomer is completed by washing the wet cake with deaerated deionized water, and, finally, flushing with hot nitrogen and drying. The M5 Monomer when dry typically has very good quality and stability. Using this monomer, poly(2,3,5,6-tetraminopyridine-co-2,5-dihydroxyterephthalate) (M5 Polymer) is prepared using the following steps. A slurry is prepared from the tetraminopyridinium dihydroxyterephthalate and polyphosphoric acid. The slurry so obtained is homogenized at about 100° C. for about 1 hour. Stirring of the mixture is continued at about 140° C. for about 1 hour. The temperature is rapidly increased to about 180° C. to dissolve the remaining dipotassium 2,5-dihydroxyterephthalic acid, then is polymerized at about 180° C. for about 0.3 to about 2.5 hours, preferably for about 1 to about 2.5 hours. The polymer is prepared in concentrations in the range of from about 10 to about 21 weight %. For higher molecular weight, the concentration of the polymer in the polyphosphoric acid solution is preferably lower, such as from about 14 to about 18 weight %. For subsequent spinning of yarns, the concentration is preferably in the range of from about 12 to about 19 weight %.

The mixture obtained from the polymerization reaction is used directly for spinning or extrusion into fibers, films, or tapes. To obtain a solution that can be spun or extruded directly it is desired that the concentration of $P_2O_5$ in the $P_2O_5/H_2O$ solvent system is at least 79.5% by weight to 84% by weight after the reaction has ended. At a concentration of more than 84% by weight it can be necessary to under some circumstances to have a chain terminator such as benzoic acid present during the polymerization reaction in order to prevent the viscosity from rising too high. The final step involves extraction of the fibers, films, or tapes using sequentially water, ammonium hydroxide solution, and water. Further details on preparation of fibers, films or tapes are provided in U.S. Pat. No. 5,674,969.

While batch processes are described above, and in the Examples below, for the processes of the present invention, the invention further includes continuous processes for the manufacture of larger product quantities. Continuous processes typically provide tighter control of reaction conditions, for instance temperature. Continuous processing thus results in improved product quality, improved product consistency, and economic benefits.

In a further embodiment, the nitration process of the present invention is applicable to other nitrations. For instance, it is also beneficial to the nitration of diaminobenzenes, particularly m-diaminobenzene. In the case of m-diaminobenzene, there are similar improvements in the quality of the 1,3-diamino-4,6-dinitrobenzene produced. The latter compound can be similarly reduced to 1,2,4,5-tetraminobenzene, an intermediate for the preparation of a similar rigid rod copolymer, poly(1,2,4,5-tetraminobenzene-co-2,5-dihydroxyterephthalate). The end-product copolymer thus produced has improved tenacity and inherent viscosity.

The processes of the present invention are useful to prepare diaminodinitropyridine and diaminodinitrobenzene that contains less than about 0.1% by weight of undesired intermediates. Such diaminodinitropyridine and diaminodinitrobenzene are useful in the process of the present invention to make rigid rod polymers having an inherent viscosity of less than about 25 dL/g.

Materials and Test Methods

The following materials and test methods were used in the Examples herein.

1) Nitric acid (98%) was obtained from El Dorado Chemical Company, El Dorado Ark.

2) 2,6-Diaminopyridine (DAP) was obtained from Alkali Metals, Inc. of Hyderabad, India.

3) 20% Oleum was obtained from E. I. du Pont de Nemours and Company, Wilmington Del.

4) Dipotassium 2,5-dihydroxyterephthalate

Dipotassium 2,5-dihydroxyterephthalate was prepared in the known "Kolbe-Schmidt" type reaction from hydroquinone. Hydroquinone was mixed with potassium carbonate and potassium formate, the latter which acted as a solvent when molten. The mixture was heated to 200° C. with stirring to provide a homogeneous solution. Excess carbon dioxide was bubbled through the stirred solution for about 8 h. Excess carbon dioxide optionally may be recycled. The reaction mass was drowned in water, and filtered. When the drowned and stirred reaction mass was filtered, the sparingly soluble dipotassium 2,5-dihydroxyterephthalate was separated from water-soluble potassium formate and potassium carbonate.

5) 2,6-Diaminopyridine hemisulfate (DAPH)

2,6-Diaminopyridine hemisulfate (DAPH) was prepared as follows. To a 5-L round-bottomed flask equipped with a means of temperature control and a liquid addition funnel was added water (deionized, 2 L) and 2,6-diaminopyridine (DAP 500 g) and the mixture stirred to form a solution. Sulfuric acid (96%, 334 g) the stoichiometric amount) was added at a rate to raise and then to maintain a temperature of 45° to 55° C. An exotherm resulted when the sulfuric acid was added. The solution became brown during the reaction, probably due to the generation of small quantities of water-soluble oxidation products of DAP. Off-white crystals of 2,6-diaminopyridene hemisulfate (DAPH or DAP.½$H_2SO_4$) precipitated out as the sulfuric acid was added. The end-point pH was adjusted to between about pH 3 to about pH 5, preferably to a pH about 4. Any necessary final adjustment was by small supplemental additions of sulfuric acid to lower the pH or by small supplemental additions of DAP to raise the pH. The reaction mixture was then cooled to room temperature and filtered. The wet crystalline filter cake was washed once with water (800 mL) and once with industrial denatured 2 T ethanol (ethanol denatured with 7.5% toluene and containing 7.5% water) or water (800 mL). The crystals were then dried in a vacuum oven at 75° C. and 30.5 kPa. At 25° C., the solubility of DAP Hemisulfate in water was about 1.5% and in ethanol less than 0.15%. Thus, in a series of preparations, the water filtrate and washes, which contained small amounts of dissolved DAPH, optionally may be reused in subsequent preparations to maximize yield. With this recycle, the yield of DAPH was 98-99%.

6) DARCO G60 is an activated carbon powder for removing colors from liquids and was obtained from Sigma-Aldrich, Milwaukee, Wis.

7) The water used in all examples was deionized water.

Test Method 1. Measurement of Inherent Viscosity

The inherent viscosities (IV) of M5 Polymers were determined using viscosity measured with a Viscotek Forced Flow Viscometer Y900 (Viscotek Corporation, Houston, Tex.) for the polymer dissolved in 50/50 weight % trifluoroacetic acid/methylene chloride at a 4 g/L concentration at 19° C. following an automated method based on ASTM D 5225-92. The measured IV values of M5 Polymer were correlated to IV values measured manually in 60/40 weight % phenol/1,1,2,2-tetrachloroethane following ASTM D 4603-96.

Test Method 2. Tenacity

The physical properties of the yarns reported in the following examples were measured using an Instron Corp. Tensile Tester, Model No. 1122 (Instron Corp., Canton Mich.). Specifically, tenacity was measured according to ASTM D-2256.

EXAMPLES

Example 1

To a 3-L round-bottomed flask, equipped with a mechanical stirrer, a moisture trap, a thermocouple, and a dry-ice/acetone bath for cooling, was added 20% oleum (containing 20% sulfur trioxide in sulfuric acid, 1350 g). The acid in the flask was cooled to 10° C. 2,6-diaminopyridine hemisulfate (DAPH, 316.4 g, 2 mole, prepared from DAP) was added in portions over 30 min., maintaining the temperature at 15-25° C. The reaction mass was then stirred at 15° C. until the solids dissolved to give a dark brown homogeneous solution. The solution was then cooled to 0° C. and 98% nitric acid (270 g, 5% excess), was added drop-wise while maintaining the temperature below 15° C. The nitration product was stirred for 2 hours at 21° C. after the completion of the nitric acid addition, and then quenched in dilute sulfuric acid solution as described below.

To a 12-L round-bottomed flask equipped with a mechanical stirrer, an overhead condenser, a thermocouple, a dry-ice/acetone bath for cooling, and an addition funnel, was added 20% sulfuric acid (6.7 kg). When practical, the 20% sulfuric acid was prepared by recycling and diluting the mother liquor from the previous nitration. This acid solution was cooled to −5° C. to −10° C. and the nitration product prepared above was added drop-wise through the addition funnel while maintaining the temperature in the 12-L flask below −5° C. Bright yellow crystals of 2,6-diamino-3,5-dinitropyridine (DADNP) precipitated. After the completion of this addition, de-ionized water (1 L) was added, the mixture was brought to room temperature, and stirred at room temperature for 1 h. The DADNP slurry was filtered in a fritted glass filter and the wet cake was washed with water (1 L) at room temperature three times. The filter cake was washed sequentially with deionized water, 5% aqueous NH₃ solution, and then deionized water. Each wash was between about 5 to about 10 times the weight of the initial 2,6-diaminopyridine). The crude DADNP (360 g, 90% yield) contained 1.05% HADNP and non-detectable (less than 0.05%) DANPS by HPLC.

The crude DADNP sample was combined with another smaller sample from a similar experiment and the combined DADNP sample (474 g) and was again purified by stirring it in THF (1 L) and aqueous ammonia (1.3 L, 7% ammonia) at 50° C. over the weekend (2 days). The wet cake was washed with water (two 500-mL portions) and dried in a vacuum oven at 85° C. to a constant weight to obtain bright yellow, fluffy DADNP (460 g, 97% purification yield). An HPLC analysis gave 0.5% HADNP, DANPS was undetectable, whereas $^1$H NMR analysis showed no HADNP or sulfuric acid.

A sample of the purified DADNP (97 g, 0.49 mole), prepared as described above, was converted to 2,3,5,6-tetraminopyridine (TAP) by hydrogenation. The DANDP was placed in a 1-L autoclave with de-aerated and deionized water (500 g), 5% supported Pt catalyst (Degussa F101, 1 g dry basis), and ammonia gas (10 g). After closing and inerting the autoclave, the slurry was warmed to 65° C. and treated with hydrogen gas bubbled into the reaction mass at 65° C. and 125 psig (kPa) until hydrogen uptake stops (typically 1 to 2 h). The highly oxygen-sensitive aqueous TAP solution (10 to 12%) was purified under a nitrogen blanket in situ using activated carbon (DARCO G60, 10 g) and was filtered into a basic aqueous (pH 9-10) solution of dipotassium 2,5-dihydroxyterephthalate (K₂-DHTA, 126 g, 0.47 mole, in 2.2 L deaerated deionized water). The autoclave was rinsed twice, each rinse using deaerated deionized water (100 g), and the washings added to the filtrate.

The entire following process steps of titration, filtration, washing, and drying, were conducted under a nitrogen atmosphere free of oxygen.

The basic TAP/K₂-DHTA solution (3 L) and 25% phosphoric acid (200 mL) solution were slowly and simultaneously fed to a jacketed and agitated glass reactor containing water (700 mL), maintaining the pH at 4.5 and the temperature at 50° C. This titration resulted in the instantaneous formation of bright yellow crystals of the TAP/K₂-DHTA complex (the M5 Monomer for making the M5 Polymer). The TAP/K₂-DHTA complex slurry was filtered in a sintered glass filter and washed sequentially with de-aerated water (three 400 mL portions) and de-aerated ethanol (two 100 mL portions). The wet cake was dried on the filter overnight under a nitrogen purge to obtain pale yellow TAP/K₂-DHTA complex (151 g, 93% yield).

A portion of the TAP/K₂-DHTA complex was then polymerized. Using this complex, the M5 Polymer was prepared using the following steps. (i) A slurry was prepared from the tetraminopyridinium dihydroxy terephthalate complex (23 g) and polyphosphoric acid (135 g). (ii) The slurry so obtained was homogenized at about 100° C. for 1 h. (iii) Stirring of the mixture was continued at 140° C. for 1 h. (iv) The temperature was rapidly increased to 180° C. to dissolve the remaining dipotassium 2,5-dihydroxyterephthalic acid, then polymerized at about 180° C. for 0.3 to 2.5 h, to obtain an M5 Polymer with an inherent viscosity (IV) of 32 dL/g.

Another portion of the purified DADNP (97 g) was hydrogenated and then coupled with K₂-DHTA (126 g) to obtain pale yellow TAP/K₂-DHTA complex (154 g, 94% yield). A small portion (23 g) of this TAP/K₂-DHTA complex was again polymerized to obtain M5 Polymer having an IV of 31 dL/g. The remaining of the two TAP/K₂-DHTA complex samples (250 g) were combined and the combined sample was polymerized as a large batch in the presence of 0.7% chain terminator (o-phenylenediamine) to obtain M5 Polymer having an IV of 26 dL/g and a tenacity of 32 g (force)/denier. Note that the intentional use of a chain terminator reduces the IV of the polymer, but the resulting fiber is of superior quality. Example 1 showed the formation of DADNP which was free of DANPS from DAPH by the process of the present invention, resulting in good quality TAP and thus good quality M5 Polymer, the latter having an IV higher than 25 dL/g and a tenacity greater than 30 g (force)/denier.

Comparative Example A

In Comparative Example A, DADNP was prepared from DAPH using a prior art method. To a 3-L round-bottomed flask, equipped with a mechanical stirrer, a moisture trap, a thermocouple, and a dry-ice/acetone bath for cooling, was added 20% oleum (containing 20% sulfur trioxide in sulfuric acid, 1350 g). The acid in the flask was cooled to 10° C. 2,6-diaminopyridine hemisulfate (DAPH, 237.3 g, 1.5 mole, prepared as described above from DAP) was added in portions over 30 min., maintaining the temperature at 15-25° C. The reaction mass was then stirred at 15° C. until the solids dissolved to give a dark brown homogeneous solution. The solution was then cooled to 0° C. and 98% nitric acid (197 g, 2.06 mole, 2% excess), was added drop-wise while maintaining the temperature below 15° C. The nitration product was stirred only for 15 min. and then quenched in dilute sulfuric acid solution as described below.

To a 12-L round-bottomed flask equipped with a mechanical stirrer, an overhead condenser, a thermocouple, a dry-ice/acetone bath for cooling, and an addition funnel, was added 20% sulfuric acid (5.0 kg). When practical, the 20% sulfuric acid was prepared by recycling and diluting the mother liquor from the previous nitration. This acid solution was cooled to −5° C. to −10° C. and the nitration product prepared above was added drop-wise through the addition funnel while maintaining the temperature in the 12-L flask below −5° C. Bright yellow crystals of 2,6-diamino-3,5-dinitropyridine (DADNP) precipitated. After the completion of this addition, de-ionized water (1 L) was added, the mixture was brought to room temperature, and stirred at room temperature for 1 h. The DADNP slurry was filtered in a Buchner filter and the wet cake was washed with water (1 L) at room temperature. The wet cake in the Buchner filter was partially dried by vacuum suction under a nitrogen atmosphere and then dried to a constant weight in a vacuum oven at 75° C. and 30.5 kPa to obtain yellow solids of crude DADNP (293 g, 98% yield). $^1$H NMR analysis showed the sample contained 2.2% 2-hydroxy-6-amino-3,5-dinitropyridine (HADNP) and 2.2% H₂SO₄. A base titration showed that the DADNP obtained in this experiment contained 3.5% H₂SO₄. As described previously, the higher titration analysis, but not the NMR analysis, includes the sulfate equivalent of any contaminating DANPS. In a similar repeated example, yellow solid crude DADNP (285 g, 95% yield) was obtained. $^1$H NMR analysis showed the sample contained 2.7% HADNP and 4.5% H₂SO₄, demonstrating the reproducibility of the synthesis. Based on analysis of a composite sample from several repeated syntheses, the average DANPS content was about 2 to about 4%.

A composite sample of crude DADNP from above (830 g, containing about 3% HADNP) was placed in a 12-L round-bottomed flask. Tetrahydrofuran (2.2 L) and 30% aqueous ammonia (600 mL) were added to the composite sample. The mix was stirred to form a slurry and stirred overnight at 45° C. before filtering in a Buchner filter at room temperature. The wet cake on the filter was washed with water (four portions of 250 mL) at room temperature and partially dried by vacuum suction under a nitrogen atmosphere. The cake was then dried to a constant weight in a vacuum oven at 75° C. and 30.5 kPa to obtain bright yellow solids of purified DADNP (800 g, 96% purification yield). $^1$H NMR analysis showed the sample contained 0.1% HADNP and 0.05% $H_2SO_4$. A base titration showed that the sample contained 0.4% $H_2SO_4$. Another analysis by HPLC showed the sample contained 0.3% HADNP and 0.8% DANPS.

A sample of the purified DADNP (100 g), prepared as described above, was converted to 2,3,5,6-tetraminopyridine (TAP) by hydrogenation. DANDP (100 g) was placed in a 1-L autoclave with de-aerated and deionized water (500 g), 5% supported Pt catalyst (Degussa F101, 1 g dry basis), and ammonia gas (10 g). After closing and inerting the autoclave, the slurry was warmed to 65° C. and treated with hydrogen gas bubbled into the reaction mass at 65° C. and 125 psig (963 kPa) until hydrogen uptake stops (typically 1 to 2 h). The highly oxygen-sensitive aqueous TAP solution (10 to 12%) was purified under a nitrogen blanket in situ using activated carbon (DARCO G60, 10 g) and was filtered into a basic aqueous (pH 9-10) solution of di-potassium 2,5-dihydroxy-terephthalate ($K_2$-DHTA, 126 g in 2.2 L deaearated deionized water). The autoclave was rinsed twice, each rinse using deaerated DI water (100 g), and the washings added to the filtrate.

The entire following process steps of titration, filtration, washing, and drying, were conducted under a nitrogen atmosphere free of oxygen. The TAP/$K_2$-DHTA complex was oxygen sensitive and discolored to orange and then light brown within a week if exposed to air. The basic TAP/$K_2$-DHTA solution (3 L) and 25% phosphoric acid (200 mL) solution were slowly and simultaneously fed to a jacketed and agitated glass reactor containing water (700 mL), maintaining the pH at 4.5 and the temperature at 50° C. This titration resulted in the instantaneous formation of bright yellow crystals of the TAP/$K_2$-DHTA complex (the M5 Monomer for making the M5 Polymer). The TAP/$K_2$-DHTA complex slurry was filtered in a sintered glass filter and washed sequentially with de-aerated water (three 400 mL portions) and de-aerated ethanol (two 100 mL portions). The wet cake was dried on the filter overnight under a nitrogen purge to obtain pale yellow TAP/$K_2$-DHTA complex (157 g, 96% yield). The ratio of TAP to $K_2$-DHTA contained about a 3% to about a 5% excess of TAP. This small excess of TAP was removed in the washing step, and prevented the presence of any excess DHTA (free acid) that would otherwise precipitate out with the TAP/$K_2$-DHTA complex.

The TAP/$K_2$-DHTA complex was then polymerized using the procedure described in Example 1. Using this complex, the M5 Polymer was prepared using the following steps. (i) A slurry was prepared from the tetraminopyridinium dihydroxyterephthalate (23 g) and polyphosphoric acid (135 g). (ii) The slurry so obtained was homogenized at about 100° C. for 1 h. (iii) Stirring of the mixture was continued at 140° C. for 1 h. (iv) The temperature was rapidly increased to 180° C. to dissolve the remaining dipotassium 2,5-dihydroxyterephthalic acid, then polymerized at about 180° C. for 0.3 to 2.5 h, to obtain an M5 Polymer with an inherent viscosity (IV) of 22 dL/g. The presence of measurable quantities of DANPS resulted in poor quality TAP, and poor quality M5 Polymer. In a similar example, the same purified DADNP was used to obtain another TAP/$K_2$-DHTA complex sample that was initially light orange in color when dried (152 g, 93% yield) that yielded M5 Polymer with a lower IV of 17 dL/g. The discoloration and lower IV, believed to be due to inadvertent contact with air, emphasizes importance of oxygen exclusion. As indicated above, acceptable M5 Polymer has an IV not less than 25 dL/g.

Comparative Example B

In Comparative Example B DADNP was prepared from DAP using a prior art process. The nitration experiment described in Comparative Example A was repeated except for replacing the DAPH (1.5 mole) with DAP (2,6-diaminopyridine, 163.7 g, 1.5 mole, to obtain yellow crude DADNP (277 g, 93% yield). $^1$H NMR analysis showed the sample was identical to that obtained using DAPH in Comparative Example A and contained 2% HADNP and 1.4% $H_2SO_4$. A subsequent HPLC analysis showed that this sample contained 2.8% DANPS.

Comparative Example B was duplicated at one-third scale (DAP, 54.55 g, 0.5 mole) in 1-L (nitration) and 3-L flasks (quench), respectively. The yellow crude DADNP (94 g, 94%) obtained in this smaller scale experiment contained 2.6% HADNP and 1% sulfuric acid as determined by $^1$H NMR. HPLC analysis showed that the sample contained 2.5% DANPS.

Crude DADNP samples prepared from DAP were combined and purified using THF and aqueous ammonia as described in Comparative Example A to obtain purified DADNP (950 g) containing 0.3% HADNP and 0.7% $H_2SO_4$. An HPLC analysis showed that it also contained 0.5% DANPS.

Purified DADNP (100 g) from above was used as described in Comparative Example A to make sequentially pale yellow TAP/$K_2$-DHTA complex (152 g, 91%) and M5 Polymer. The M5 Polymer had an IV of 23 dL/g.

Example 2

DADNP (400 g), prepared according to the procedure of Example 1 and containing 1.1% DANPS and 0.3% HADNP as determined by HPLC, was dissolved in portions in a mixture of 96% $H_2SO_4$ (1.125 kg) and 20% oleum (1.125 kg) in a 3-L round-bottomed flask. The temperature was maintained between 0° to 10° C. The mixture was stirred until all solids dissolved. To this solution was added 98% $HNO_3$ (15 g) drop-wise at 0-10° C. The brown to burgundy color solution was stirred for an additional 4 h at 10° C. The mixture was added to a 20% $H_2SO_4$ solution (10.4 kg) at 0±2° C. in a 12-L round-bottomed flask as described in Example 1. A bright yellow slurry was obtained. The slurry was stirred, diluted with 1.67 kg deionized water, filtered and washed with three 1.67 kg washes, the first and third washes being deionized water, the second wash was again 5% aqueous ammonia, using a fritted-glass filter as described in Example 1. Bright yellow DADNP (389 g) was obtained after drying. HPLC analysis showed the sample contained 0.7% HADNP and no detectable DANPS.

The crude DADNP sample from above was combined with other similar DADNP samples and again purified by stirring it in proportional amounts of THF and aqueous ammonia as described in Example 1, and was dried to obtain bright yellow, fluffy DADNP. An HPLC analysis gave 0.4% HADNP, undetectable DANPS, whereas $^1$H NMR analysis showed 0.5% HADNP and 0.07% sulfuric acid.

A portion of the purified DADNP from above (130 g, 0.65 mole) was hydrogenated according to the hydrogenation procedure of Example 1. The resulting aqueous TAP solution was first color treated with DARCO G60 (15 g), then complexed with $K_2$-DHTA (165 g, 0.60 mole, prepared as in Example 1 to obtain pale yellow TAP/K$_2$-DHTA complex (209 g, 98% yield). A portion of this TAP/K$_2$-DHTA complex was polymerized as described in Example 1 to obtain M5 Polymer having an IV of 31 dL/g. Another portion of the same purified DADNP (130 g) was hydrogenated and then coupled with K$_2$-DHTA (165 g) to obtain pale yellow TAP/K$_2$-DHTA complex (209 g, 98% yield). A small portion of this TAP/K$_2$-DHTA complex was polymerized to obtain a high quality M5 Polymer with an IV of 29 dL/g.

Using the procedure described above, the starting DADNP for this example containing 1.1% DANPS and 0.3% HADNP was also hydrogenated and then coupled with K$_2$-DHTA to make TAP/K$_2$-DHTA complex. A portion of that TAP/K$_2$-DHTA complex was polymerized as described in Example 1 to obtain M5 Polymer with a sub-standard IV of 23 dL/g, demonstrating the increase in IV associated with the purification of the DADNP. Example 2 demonstrated that DADNP, containing DANPS in excess of 0.1%, can be further nitrated to convert the DANPS impurity to DADNP, resulting in good quality TAP and thus good quality M5 Polymer Example 3

The same procedure of removing DANPS by re-nitration as described in Example 2 was repeated using DADNP (500 g) containing 1% DANPS and 1.5% HADNP to obtain crude re-nitrated DADNP (473 g, 95%) containing 2.2% HADNP and no detectable DANPS. A portion of this re-nitrated crude DADNP (53 g) was again hydrogenated and the resulting aqueous TAP solution was coupled with K$_2$-DHTA (63 g, 0.23 mole) to obtain pale yellow TAP/K$_2$-DHTA complex (80 g, 98% yield) using the procedure as described in Example 1. A portion of this TAP/K$_2$-DHTA complex was polymerized as in Example 1 to obtain M5 Polymer having an IV of 24 dL/g. A portion of the re-nitrated crude DADNP (200 g) was then dissolved in hot DMAC (1.2 L) and then treated with 5% aqueous K$_2$CO$_3$ solution (100 mL) to remove HADNP. A purified DADNP (187 g, 96%), containing 100% DADNP and no HADNP and no DANPS was obtained. A portion of this pure DADNP (50 g) was hydrogenated and then coupled with K$_2$-DHTA (63 g, 0.23 mole) as described in Example 1 to obtain pale yellow TAP/K$_2$-DHTA complex (78 g, 95% yield). A portion of this TAP/K$_2$-DHTA complex was polymerized as described in Example 1 to obtain M5 Polymer IV of 31 dL/g. For comparison, the starting DADNP containing 1% DANPS and 1.5% HADNP, when eventually converted to TAP/K$_2$-DHTA complex and then polymerized, had yielded an IV of 17 dL/g. Example 3 demonstrated that DADNP containing DAN PS in excess of 0.1% that resulted in M5 Polymer with IV less than 25 dL/g, can be renitrated to remove the contaminating DANPS. Renitrated DADNP can be converted to M5 Polymer with acceptable IV.

Example 4

The same procedure of removing DANPS by re-nitration as described in Example 2 was repeated a third time using DADNP (400 g) containing 4% DANPS and 3.5% HADNP to obtain crude re-nitrated DADNP (380 g, 95%) containing 3.2% HADNP and no detectable DANPS. This re-nitrated crude DADNP (379 g) was treated with 5% aqueous K$_2$CO$_3$ solution (100 mL) to remove HADNP, and a purified DADNP (356 g, 94%), containing 99.7% DADNP, 0.2% HADNP and no DANPS, was obtained. A portion of this pure DADNP (50 g) was hydrogenated and then coupled with K$_2$-DHTA (63 g, 0.23 mol) as described in Example 1 to obtain pale yellow TAP/K$_2$-DHTA complex (798 g, 97% yield). A portion of this TAP/K$_2$-DHTA complex was then polymerized as described in Example 1 to obtain M5 Polymer having an IV of 31 dL/g. Example 4 demonstrated that DADNP containing DANPS in excess of 0.1% that resulted in M5 Polymer with IV less than 25 dL/g, can be renitrated to remove the contaminating DANPS. Renitrated DADNP can be converted to M5 Polymer with acceptable IV.

Example 5 and Comparative Example C

The nitration of DAPH, as described in Example 1, was repeated using half the recipe of ingredients. For example, DAPH (158.2 g, 1 mole), prepared as described above using DAP, was used. Similarly, 20% oleum (900 g), 98% HNO$_3$ (135 g) were used in the same equipment. The same procedure described in Example 1 was used until the end of nitration. After the nitration, the reaction mixture (1.19 kg) was stirred for 15 minutes and then split into two halves. The first half (Comparative Example C, 596 g) of the nitration reaction product was quenched immediately at 0±2° C. into 1.675 kg of 20% H$_2$SO$_4$ solution. To this solution was then added 250 g of deionized water to complete the DADNP product precipitation. The product was then filtered and washed three times using water (300 g), 5% NH$_3$ solution (300 g), and then water (300 g). The crude DADNP (82 g, 82% yield) contained 1.2% HADNP and 10.3% DANPS by HPLC. The second half of the nitration reaction mixture (Example 5, 596 g) was stirred at 20-23° C. for an additional 2.5 h. The same procedure, as in the first half of the reaction mixture, was used to obtain crude DADNP (93 g, 93% yield) containing 0.5% HADNP and non-detectable (less than 0.05%) DANPS by HPLC.

Example 6 and Comparative Example D

The experiment described in Example 5 was repeated using DAP (109.1 g, 1 mole) instead of DAPH. Otherwise, the same equipment and procedure were used. After the nitration, the reaction mass (1.144 kg) was stirred for 30 minutes to provide a nitration product and then split into two halves. The first half (Comparative Example D, 570 g) of the nitration product was quenched immediately at 0±2° C. into 1.675 kg of 20% H$_2$SO$_4$ solution. To this solution was then added 250 g of deionized water to complete the DADNP product precipitation. The product was then filtered and washed three times using water (300 g), 5% NH$_3$ solution (300 g), and then water (300 g). The crude DADNP (87 g, 88% yield) contained 0.9% HADNP and 5.1% DANPS by HPLC. The second half of the nitration product (Example 6, 596 g) was stirred at 20-23° C. for an additional 2 h. The same procedure, as in the first half of the reaction mixture, was used to obtain crude DADNP (92 g, 92% yield) containing 0.3% HADNP and undetectable (less than 0.05%) DANPS by HPLC.

A portion of the crude DADNP (50 g, 0.25 mole), from the first half (Comparative Example D) of the nitration product described above (with 30-min stirring), was hydrogenated and the resulting aqueous TAP solution was first color treated with DARCO G60 (5 g) and then coupled with K$_2$-DHTA (63 g, 0.23 mole) as described in Example 1 to obtain pale yellow TAP/K$_2$-DHTA complex (74 g, 91% yield). A portion of this TAP/K$_2$-DHTA complex was polymerized as described in Example 1 to obtain a low polymer IV of 16 dL/g.

A portion of the crude DADNP (51 g, 0.26 mole), from the second half (Example 6) of the nitration product described above (a total of 2.5 h of stirring), was hydrogenated and the resulting aqueous TAP solution was first color treated with DARCO G60 (5 g) and then coupled with K$_2$-DHTA (63 g, 0.23 mole) as described in Example 1 to obtain pale yellow TAP/K$_2$-DHTA complex (78 g, 96% yield). A portion of this TAP/K$_2$-DHTA complex was polymerized as described in Example 1 to obtain an excellent M5 Polymer with an IV of 32 dL/g. In strength tests, polymer samples with IV of 32 dL/g resulted in high quality fiber, exceeding breaking strength of 40 g (force)/denier.

Example 7 and Comparative Example E

The procedure of Example 5 was repeated using DAP (163.65 g, 1.5 mole). The same procedure and proportionately same amounts of 20% oleum (1.35 kg) and 98% nitric acid (202.5 g, 3.15 mole, 5% excess) were used.

After the nitration, the nitration product (1.716 kg) was stirred for 35 minutes and then split into two halves. The first half (Comparative Example E, 850 g) of the nitration product was quenched immediately at 0±2° C. into 2.5 kg of 20% H$_2$SO$_4$ solution. To this solution was then added 375 g of deionized water to complete the DADNP product precipitation. The product was then filtered and washed three times using water (500 g), 5% NH$_3$ aqueous solution (500 g) and then water (500 g). The crude DADNP (136 g, 92% yield) contained 0.6% HADNP and 2.5% DANPS by HPLC. The second half of the nitration product (Example 7, 858 g) was stirred at 5-10° C. for an additional 2 h. The same procedure, as for the first half of the nitration product, was used to obtain crude DADNP (140 g, 93% yield) containing 0.5% HADNP and 0.3% DANPS by HPLC. The crude DADNP (135 g) from the second half of the nitration product (Example 7 with 2.5 h of stirring) was purified by dissolving it in a 3-L round-bottom flask using 1.2 L of hot DMF (140° C.) and then re-precipitating it by cooling the solution to obtain purified DADNP (130 g, 96% yield) with 0.2% HADNP, no DANPS, and 99.7% DADNP.

A portion of the crude DADNP (50 g, 0.25 mole), from the first half (Comparative Example E) of the nitration product described above (35-min. stirring), was hydrogenated and the resulting aqueous TAP solution was first color treated with DARCO G60 (5 g) and then coupled with K$_2$-DHTA (63 g, 0.23 mole) as described in Example 1 to obtain pale yellow TAP/K$_2$-DHTA complex (76 g, 93% yield). A portion of this TAP/K$_2$-DHTA complex was polymerized as described in Example 1 to obtain a polymer with a low IV of 17 dL/g.

A portion of this Example 7 DMF-purified DADNP (50 g, 0.25 mole) was hydrogenated and the resulting aqueous TAP solution was first decolorized with DARCO G60 (5 g) and then coupled with K$_2$-DHTA (63 g, 0.23 mole) as described in Example 1 to obtain pale yellow TAP/K$_2$-DHTA complex (78 g, 96% yield). A portion of this TAP/K$_2$-DHTA complex (25 g) was polymerized as described in Example 1 to obtain an excellent M5 Polymer with an IV of 33 dL/g. In strength tests, polymer samples with IV of 33 dL/g resulted in high quality fiber, exceeding a breaking strength of 42 g (force)/denier.

Table 2 summarizes the data from Examples 1 to 7 and Comparative Examples A to E.

TABLE 2

| Ex. # | Method | DANPS | M5 Polymer IV (dL/g)* | Tenacity** |
|---|---|---|---|---|
| A | Prior art nitration of DAPH | 0.8% | 22 | (a) |
| B | Prior art nitration of DAP | 0.5% | 23 | (a) |
| 1 | Nitration of DAPH by the process of the present invention | ND | 26 | 32 |
| 2 | Renitration of poor quality DADNP prepared according to the process of Comparative Example A, contaminated with 1.1% DANPS | ND | 29 | (a) |
| 3 | Renitration of DADNP contaminated with 1% DANPS | ND | 31 | (a) |
| 4 | Renitration of DADNP contaminated with 4% DANPS | ND | 31 | (a) |
| C | Short (0.25 h) nitration mix time for DAPH | 10.3 | Not polymerized | |
| 5 | Long (2.75 h) nitration mix time for DAPH | ND | Not polymerized | |
| D | Short (0.5 h) nitration mix time for DAP | 5.1 | 16 | (a) |
| 6 | Long (2.5 h) nitration mix time for DAP | ND | 32 | (a) |
| E | Short (0.5 h) nitration mix time for DAP | 2.5 | 17 | — |
| 7 | Long (2.5 h) nitration mix time for DAP | ND | 33 | 42 |

*Acceptable quality M5 Polymer has an IV of at least 25 dL/g.
**Tenacity in g (force)/denier.
(a) not measured.
ND not detectable (detection limit for DANPS by HPLC is about 0.05%)

The data in Table 2 demonstrates the following. Comparative Examples A and B showed that the nitration method of the prior art forms sufficient DANPS in the DADNP to adversely affect the quality of M5 Polymer prepared therefrom in terms of low IV. Example 1 showed the longer nitration process of the present invention provides DADNP with much lower DANPS content and, subsequently, high quality M5 Polymer. Examples 2, 3, and 4 showed that DADNP containing harmful levels of DANPS can be renitrated to reduce the DANPS content and yield high quality M5 Polymer. Duplicating the nitration step, however, is not preferred. The short nitration times used in Comparative Examples C, D and E were compared with the longer nitration times of the present invention used in Examples 5, 6 and 7. The longer nitration times correlated with decreased DANPS contamination and higher IV values in the resulting M5 Polymer.

Example 8

Example 8 demonstrated the preparation of DANPS from DAPH. To a 1-L round-bottomed flask, equipped with a mechanical stirrer, a moisture trap, a thermocouple, and a dry-ice/acetone bath for cooling, was added 20% oleum (fuming sulfuric acid containing 20% dissolved SO$_3$, 450 g). The acid in the flask was cooled to 0° C. 2,6-diaminopyridine hemi-sulfate (DAPH, 79.1 g, 0.5 mole), prepared in-house using 2,6-diaminopyridine (DAP) was added in portions over 30 minutes while maintaining the temperature at 0-10° C. The reaction mass was stirred at 15° C. until the solids dissolved to give a dark brown homogeneous solution. The solution was then cooled to 0° C. and 98% nitric acid (33 g, 0.51 mole, 2% excess), was added drop-wise over 45 minutes while maintaining the temperature below 10° C. The sample was stirred for an additional 2 h and was quenched in dilute sulfuric acid solution as described below.

To a 3-L round-bottomed flask equipped with a mechanical stirrer, an overhead condenser, a thermocouple, and a dry-ice/acetone bath for cooling, was added 20% sulfuric acid (1.7 kg) solution. This acid solution was cooled to 0° C. and the nitration reaction mass from the 3-L round-bottom flask from above was added drop-wise over 1.5 h through a liquid-addition funnel while maintaining the temperature in the 3-L flask below 2° C. Bright yellow crystals of product precipitated in the 3-L flask. After the completion of this addition, de-ionized water was added (250 mL), the mixture was brought to the room temperature, and was stirred at room temperature for 1 h. The bright yellow slurry was filtered in a fritted-glass filter and the wet cake was washed three times at room temperature, first with water (300 g), the second time with 5% aqueous $NH_3$ solution (300 g) and the third time with water again (300 g). Each wash involved making slurry of the wet cake, stirring for 15 min. and then filtering. The wet cake in the filter was partially dried by nitrogen blow and vacuum suction and then dried to a constant weight in a vacuum oven to obtain yellow solids of product (112 g, 96% yield, based on the sample being DANPS, MW=234).

An LC/MS analysis conducted on this sample showed the presence of two peaks, a minor DADNP peak having a molecular weight of 199 and a major peak having a molecular weight of 234. The isotopic distribution of the parent ion suggested the presence of sulfur in this impurity. Based on this LC/MS analysis, the most logical explanation of the 234 molecular ion peak would be 2,6-diamino-3-nitropyridine-5-sulfonic acid (DANPS). Subsequently, two-dimensional $^{13}C$ NMR confirmed that this peak was indeed DANPS. A subsequent HPLC analysis showed that the sample contained 3% DADNP, no HADNP, and 97% DANPS.

No attempt was made to hydrogenate or polymerize this sample since samples containing only a few percent DANPS resulted in severe catalyst poisoning and an unsuccessful TAP formation.

Example 9

In Example 9 DANPS was prepared from DAP. The procedure described in Example 8 was employed using the same equipment, procedure, and chemicals except for replacing DAPH (79.1 g, 0.5 mole) with DAP (54.6 g, 0.5 mole). Also, the wash size was increased to 500 g from 300 g in each of the three washes of the wet cake.

After the washes, the wet cake in the filter was partially dried by nitrogen blow and vacuum suction and then dried to a constant weight in a vacuum oven to obtain yellow solids of product (91 g, 86% yield, based on the sample being DANPS, MW=234). A HPLC analysis showed that the sample contained 3% DADNP, no HADNP, and 97% DANPS. No attempt was made to hydrogenate or polymerize this sample.

What is claimed is:

1. In a process for the preparation of 1) diaminodinitropyridine or 2) diaminodinitrobenzene by contacting 1) an aminopyridine or 2) an aminobenzene, respectively, with oleum and nitric acid, wherein the improvement comprises adding, with stirring, at least about 1% molar excess of nitric acid based upon the aminopyridine or aminobenzene respectively, and stirring is continued for about two to about four hours to form first 1) aminonitropyridine sulfonic acid or 2) aminonitrobenzene sulfonic acid, respectively, and then 1) diaminodinitropyridine or 2) diaminodinitrobenzene respectively.

2. The process of claim 1 wherein the aminopyridine or aminobenzene is contacted with oleum prior to contacting with nitric acid.

3. The process of claim 2 wherein the nitric acid is added in two separate increments.

4. The process of claim 1 wherein the molar excess of nitric acid is from about 1% to about 3%.

5. The process of claim 1 wherein the diaminodinitropyridine contains less than 0.1% by weight of 26-diamino-3-notropyridine-5-sulfonic acid.

6. The process of claim 1 wherein the diaminodinitrobenzene contains less than 0.1% by weight of 26-diamino-3-nitrobenzene-5-sulfonic acid.

7. A composition comprising 26-diamino-3-nitropyridine-5-sulfonic acid produced by the process of claim 1.

8. The composition of claim 7 prepared by contacting a diaminopyridine or diaminopyridine hemisulfate with oleum to form diaminopyridine sulfonic acid, and adding at least a 1% molar excess of nitric acid based upon the diaminopyridine to yield diaminonitropyridine sulfonic acid.

9. A process for purification of 1) diaminodinitropyridine which contains 26-diamino-3-nitropyridine-5-sulfonic acid or 2) diaminodinitrobenzene which contains 26-diamino-3-nitrobenzene-5-sulfonic acid comprising contacting 1) said diaminodinitropyridine or 2) said diaminodinitrobenzene respectively with oleum and at least about 1% molar excess of nitric acid based upon the diaminodinitropyridine or diaminodinitrobenzene, with stirring, and stirring is continued for about two to about 4 hours to yield 1) diaminodinitropyridine having less than about 0.1% by weight of 26-diamino-3-nitropyridine-5-sulfonic acid or 2) diaminodinitrobenzene having less than about 0.1% by weight of 26-diamino-3-nitrobenzene-5-sulfonic acid respectively.

10. The process of claim 9 wherein the nitric acid is added in two separate increments.

11. The process of claim 9 wherein the molar excess of nitric acid is from about 1% to about 3%.

* * * * *